US009868927B2

(12) United States Patent
Reinoso Garcia et al.

(10) Patent No.: US 9,868,927 B2
(45) Date of Patent: Jan. 16, 2018

(54) CONTAINER COMPRISING A DETERGENT COMPOSITION CONTAINING MGDA WITH AN ENANTIOMERIC EXCESS OF THE L-ISOMER

(71) Applicant: BASF SE, Ludwigshafen (DE)

(72) Inventors: Marta Reinoso Garcia, Dossenheim (DE); Thomas Schmidt, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/518,936

(22) PCT Filed: Oct. 7, 2015

(86) PCT No.: PCT/EP2015/073149

§ 371 (c)(1),
(2) Date: Apr. 13, 2017

(87) PCT Pub. No.: WO2016/058888

PCT Pub. Date: Apr. 21, 2016

(65) Prior Publication Data

US 2017/0240852 A1 Aug. 24, 2017

(30) Foreign Application Priority Data

Oct. 17, 2014 (EP) .................................... 14189418

(51) Int. Cl.

| | |
|---|---|
| ***C11D 3/33*** | (2006.01) |
| ***C07C 227/42*** | (2006.01) |
| ***C07C 229/24*** | (2006.01) |
| ***C11D 17/04*** | (2006.01) |
| ***C11D 3/37*** | (2006.01) |
| ***C11D 11/00*** | (2006.01) |
| ***C11D 3/39*** | (2006.01) |
| ***C11D 3/40*** | (2006.01) |
| ***B65D 65/46*** | (2006.01) |
| ***B65B 3/02*** | (2006.01) |
| ***B65B 7/02*** | (2006.01) |
| ***B65D 75/30*** | (2006.01) |

(52) U.S. Cl.

CPC .............. *C11D 17/045* (2013.01); *B65B 3/02* (2013.01); *B65B 7/02* (2013.01); *B65D 65/46* (2013.01); *B65D 75/30* (2013.01); *C11D 3/33* (2013.01); *C11D 3/3753* (2013.01); *C11D 3/3942* (2013.01); *C11D 3/40* (2013.01); *C11D 11/0017* (2013.01); *C11D 11/0023* (2013.01); *C11D 17/042* (2013.01); *C11D 17/043* (2013.01)

(58) Field of Classification Search

CPC ..... C11D 3/0094; C11D 3/33; C11D 11/0017; C11D 7/3245; C11D 17/042; C07C 227/42; C07C 229/24

See application file for complete search history.

(56) References Cited

U.S. PATENT DOCUMENTS

| | | | | |
|---|---|---|---|---|
| 5,849,950 | A * | 12/1998 | Greindl | C07C 227/26 562/565 |
| 8,802,894 | B2 | 8/2014 | Oftring et al. | |
| 2010/0160202 | A1 | 6/2010 | Housmekerides et al. | |
| 2010/0292120 | A1 | 11/2010 | Oehms et al. | |
| 2012/0248370 | A1* | 10/2012 | Oftring | C07C 227/26 252/182.12 |
| 2012/0283473 | A1* | 11/2012 | Oftring | C07C 227/42 562/571 |
| 2013/0206181 | A1 | 8/2013 | Giles et al. | |
| 2017/0029751 | A1* | 2/2017 | Letzelter | C11D 17/045 |

FOREIGN PATENT DOCUMENTS

| | | | |
|---|---|---|---|
| DE | 198 19 187 | A1 | 11/1999 |
| EP | 0 851 023 | A2 | 7/1998 |
| WO | 02/42400 | A2 | 5/2002 |
| WO | 03/084836 | A1 | 10/2003 |
| WO | 2007/141527 | A1 | 12/2007 |
| WO | 2009/040544 | A1 | 4/2009 |
| WO | 2009/112994 | A1 | 9/2009 |
| WO | 2011/072017 | A2 | 6/2011 |
| WO | 2012/038755 | A1 | 3/2012 |

OTHER PUBLICATIONS

International Search Report dated Dec. 8, 2015 in PCT/EP2015/073149 filed Oct. 7, 2015.
Extended European Search Report dated Apr. 2, 2015 in Patent Application No. 14189418.8.
International Preliminary Report on Patentability dated Sep. 2, 2016 in PCT/EP2015/073149.

* cited by examiner

*Primary Examiner* — Charles Boyer

(74) *Attorney, Agent, or Firm* — Oblon, McClelland, Maier & Neustadt, L.L.P.

(57) ABSTRACT

Container comprising a single unit dose of a detergent composition containing at least one complexing agent (A) dissolved in an aqueous medium, said complexing agent (A) being a mixture of the L-and D-enantiomers of methyl glycine diacetic acid (MGDA) or its respective mono-, di- or trialkali metal or mono-, di- or triammonium salts, said mixture containing predominantly the respective L-isomer with an enantiomeric excess (ee) in the range of from 5 to 85%, wherein said container is made from a polymer.

17 Claims, No Drawings

CONTAINER COMPRISING A DETERGENT COMPOSITION CONTAINING MGDA WITH AN ENANTIOMERIC EXCESS OF THE L-ISOMER

The present invention is directed towards a container comprising a single unit dose of a detergent composition containing at least one complexing agent (A) dissolved in an aqueous medium, said complexing agent (A) being a mixture of the L- and D-enantiomers of methyl glycine diacetic acid (MGDA) or its respective mono-, di- or trialkali metal or mono-, di- or triammonium salts, said mixture containing predominantly the respective L-isomer with an enantiomeric excess (ee) in the range of from 5 to 85%, wherein said container is made from a polymer.

Chelating agents such as methyl glycine diacetic acid (MGDA) and their respective alkali metal salts are useful and environmentally friendly sequestrants for alkaline earth metal ions such as $Ca^{2+}$ and $Mg^{2+}$. They can replace phosphate-type sequestrants such as sodium tripolyphosphate ("STPP"), the latter being replaced now in many countries for environmental reasons. Therefore, MGDA and related compounds are recommended and used for various purposes such as laundry detergents and for automatic dishwashing (ADW) formulations, in particular for so-called phosphate-free laundry detergents and phosphate-free ADW formulations. For shipping such chelating agents, in most cases solids such as granules are being applied or aqueous solutions.

For automatic dishwashing and laundry care, so-called single unit doses are of increased commercial importance. They are of great convenience for the end-user because such unit doses contain the right amounts of the ingredients for the washing and rinsing steps and because they can be easily placed into the automatic dishwasher or washing machine by the end-user, see, e.g., WO 2002/042400 and WO 2011/072017. Examples of unit doses are tablets and pellets and in particular pouches. Pouches in the form of multi-compartment pouches have been disclosed as well, see WO 2009/112994.

However, especially in the presence of bleaching agents on the basis of inorganic peroxides, sometimes shortcomings can be observed. Especially on long-time storing such as several months in summer, yellowing or even formation of brownish stains in the detergent compositions can be observed. Such coloring is commercially unattractive because it may suggest that the quality of the respective detergent composition may have deteriorated.

A way to avoid this shortcoming is to provide detergent compositions in containers that comprise several compartments. One compartment contains a bleaching agent and another one comprises oxidation-sensitive ingredients such as enzymes. Compartments that are removed during a washing circle can be made from polymer films, see, e.g., WO 2003/084836. Water in combinations with such films is of disadvantage, however, because it may damage said films upon storage. MGDA solutions can be provided with up to 40% by weight of MGDA at ambient temperature. Higher concentrations are not feasible. Instead, precipitation and crystallization of MGDA can be observed.

However, it is desirable that the sequestrant is provided to the washing liquor at an early stage of the wash circle. With sequestering agents such as solid MGDA, this does not work under all conditions.

It was therefore an objective of the present invention to provide a detergent composition, especially in unit dose form, that can overcome the drawbacks explained above. It was also an objective of the present invention to provide a method of manufacturing detergent compositions that can overcome the drawbacks explained above. It was further an objective to provide an element for a detergent composition that can overcome the above drawbacks, and a method for making such an element.

Accordingly, the containers comprising a single unit dose as defined at the outset have been found. They are hereinafter also being defined as containers according to the (present) invention or as inventive containers comprising a single unit dose or as inventive containers.

The inventive container is in the form of a unit dose. In the context of the present invention, the term "unit dose" refers to amounts of detergent compositions that are designed for one wash in a laundry machine or one dishwash in an automatic dishwashing machine. A unit dose may be designed for home care applications or for industrial or institutional applications, such as—but not limited to—in hospitals, canteens, restaurants, hotels, youth hostels or a commercial laundry. Preferably, unit doses in the context of the present invention are designed for home care applications. Unit doses may also be defined as single unit doses, both terms being used interchangeably in the context of the present invention.

Inventive containers comprising a single unit dose may be applied in various applications, especially for automatic dishwash or laundry applications. Depending on the application the detergent composition may contain different components besides complexing agent (A), and depending on the desired application the size may differ. It is preferred that inventive containers that are used in home care are smaller in size than inventive containers to be used in industrial or institutional applications, and it is preferred that containers used in automatic dishwash applications are smaller in size than inventive containers used in laundry cleaning applications.

In one embodiment of the present invention, inventive containers comprising a single unit dose encompass a single compartment in which all components of the respective detergent composition. In a preferred embodiment, inventive containers encompass two or more compartments, for example two, three or four compartments.

In one embodiment of the present invention inventive containers are in the form of a box with one or more compartments or in the form of a sachet with one or more compartments or in the form of a pouch with one or more compartments or in the form of a combination of a box and one or more pouches, especially in the form of the combination of a box and one pouch. In such a combination of a box and a pouch may be connected to each other, e.g., by gluing them together. A pouch with two compartments may also be referred to as two-chamber pouch. A pouch with a single compartment may also be referred to as one-chamber pouch. Thus, in particular embodiments, containers according to the present invention may be in the form of a two-chamber pouch or in the form of a combination of a box and a one-chamber pouch.

Said container may be mechanically flexible or stiff. The distinction between mechanically flexible and mechanically stiff may be made by manual determination of the degree of deformability by an average end user with two fingers. If such an average end user can deform the shape of said container by at least 5% into one dimension the respective container is deemed mechanically flexible, otherwise it is deemed stiff.

In specific embodiments, inventive containers are tablets that have at least one cavity per tablet. Per cavity there is at least one pouch, preferably there is at least one pouch placed into the cavity and attached to the tablet. In special embodiment, the volume of the pouch including the solution of complexing agent (A) corresponds to the volume of the cavity, for example they may have the same volume ±10%, preferably ±5%. The better shape and size of cavity and the pouch including the solution of complexing agent (A) correspond to each other the less breakage during transport can be observed. Such tablets may be packaged in a film of, e.g., polyvinyl alcohol. The tablet comprises components of the respective detergent composition such as surfactants, builder (s), enzymes, and/or bleaching agent.

In another specific embodiment, inventive containers are a box that has at least one cavity per box. Per cavity there is at least one pouch, preferably there is at least one pouch placed into the cavity and attached to the box. In special embodiment, the volume of the pouch including the solution of complexing agent (A) corresponds to the volume of the cavity, for example they may have the same volume ±10%, preferably ±5%. The better shape and size of cavity and the pouch including the solution of complexing agent (A) correspond to each other the less breakage during transport can be observed. The box comprises components of the respective detergent composition such as surfactants, builder(s), enzymes, and/or bleaching agent.

In another specific embodiment, inventive containers are pouches that encompass at least two compartments, for example two, three or four compartments. One of the compartments contains the solution of complexing agent (A). The other components of the respective detergent compositions are in the one or more other compartment(s).

In one embodiment of the present invention, all complexing agent (A) that is comprised in inventive containers is in the very compartment in dissolved form. In another embodiment of the present invention, a share of complexing agent (A) is comprised in one compartment in dissolved form, as stated above, and more complexing agent (A) is comprised in the other compartment or one other compartment, as applicable, of the inventive container.

Solid detergent compositions may contain residual moisture. Residual moisture refers to water other than the water that is part of the aqueous medium in which complexing agent (A) is dissolved in. In one embodiment of the present invention, the residual moisture content is in the range of from 0.1 to 10% by weight, referring to the total respective detergent composition. The residual moisture content can be determined, e.g., by Karl-Fischer-Titration or by measuring the weight loss upon drying.

In the context with the present invention, the term "pouch" refers to a container made from a flexible film. Said container is essentially closed upon storage of the respective dishwashing detergent composition. During the dishwashing process the contents of the pouch is removed from the pouch itself, preferably by dissolving the pouch.

Containers and especially pouches in the context of the present invention may have various shapes. For examples, containers may be in the form of a ball, an ellipsoid, a cube, a cuboid, or they may be of geometrically irregular shape. In special examples, pouches may have the shape of an envelope, of a pillow, of a flexible sleeve or flexible tube that is closed at both ends, of a ball or a cube.

In one embodiment of the present invention, containers according to the present invention and especially pouches have a diameter in the range of from 0.5 to 7 cm.

In one embodiment of the present invention, containers according to the present invention and especially pouches have a volume—in the closed state—in the range of from 15 to 70 ml, preferably 18 ml to 50 ml and in particular 20 to 30 ml. Such inventive containers are particularly useful for automatic dishwash in home care application. Inventive containers particularly useful for fabric care in home care applications may have a volume in the range of from 15 to 40 ml, preferably 25 to 30 ml.

In one embodiment of the present invention, each compartment has a content in the range of from 0.5 to 50 ml, preferably 5 to 25 ml. In embodiments wherein inventive containers encompass two or more compartments, such compartments may have equal size or different size. Preferably, in embodiments wherein inventive containers encompass two or more compartments, such containers encompass one major compartment and one or two or three smaller compartments.

Inventive containers are made from a polymer, preferably from a water-soluble polymer. Pouches in the context of the present invention are made from a polymer film.

Said polymer may be selected from natural polymers, modified natural polymers, and synthetic polymers. Examples of suitable natural polymers are alginates, especially sodium alginate, furthermore xanthum, carragum, dextrin, maltodextrin, gelatine, starch, and pectin. Examples of suitable modified natural polymers are methylcellulose, ethylcellulose, carboxymethyl cellulose, hydroxypropylcellulose, hydroxypropyl methyl cellulose (HPMC), and hydroxymethyl cellulose. Examples of suitable synthetic polymers are polyvinyl pyrrolidone, polyacrylamide, polyalkylene glycols, preferably polypropylene glycol and polyethylene glycol, especially polyethylene glycol with a molecular weight $M_w$ in the range of at least 2,000 g/mol, preferably of from 3,000 to 100,000 g/mol, and in particular polyvinyl alcohol.

The term "polyvinyl alcohol" as used herein does not only include homopolymers of polyvinyl alcohol that can be made by free-radical polymerization of vinyl acetate followed by subsequent hydrolysis (saponification) of all or the vast majority of the ester groups. Polyvinyl alcohol also includes copolymers obtainable by free-radical copolymerization of vinyl acetate and at least one comonomer selected from maleic acid, maleic anhydride, itaconic anhydride, methyl (meth)acrylate and 2-acrylamido-2-methyl propanesulfonic acid ("AMPS").

In a preferred embodiment of the present invention, polyvinyl alcohol as used for making containers and especially pouches has an average degree of polymerization (weight average) in the range of from 500 to 3,000 g/mol. The molecular weight $M_w$ of such polyvinyl alcohol is preferably, in the range of from 6,000 to 250,000 g/mol, preferably up to 75,000 g/mol. The molecular weight is preferably determined by gel permeation chromatography of the respective polyvinyl acetate or respective copolymer before saponification.

Preferably, polyvinyl alcohol used for making containers and especially pouches is atactic as determined by $^1$H NMR spectroscopy.

Polyvinyl alcohols used for making containers—especially pouches—essentially have repeating units of ($CH_2$—CHOH). The hydroxyl groups in polyvinyl alcohol are mostly in 1,3-position, thus forming structural units of the type —$CH_2$—CH(OH)—$CH_2$—CH(OH)—. In minor amounts (1 to 2 mole-%) there are germinal hydroxyl groups, thus forming structural units of —$CH_2$—CH(OH)—CH(OH)—$CH_2$—.

One or more modified polyvinyl alcohols may be employed as polymers instead of polyvinyl alcohol or in combination with polyethylene glycol or with polyvinyl alcohol. Examples are graft copolymers such as polyalkylene glycol grafted with polyvinyl acetate followed by subsequent hydrolysis/saponification of the ester groups.

Polymer may be used without or with one or more additives. Suitable additives are especially plasticizers such as $C_4$-$C_{10}$-dicarboxylic acids, for example adipic acid, and glycols such as ethylene glycol and diethylene glycol.

Due to their production, commercially available polyvinyl alcohols usually have residual non-saponified ester groups, especially acetate groups. Polyvinyl alcohols used for making containers and especially pouches for embodiments of the present invention essentially have a degree of saponification in the range of from 87 to 89 mole-%. The degree of saponification can be determined in accordance with the determination of the ester value, for example according to DIN EN ISO 3681 (2007-10).

In one embodiment of the present invention, polyvinyl alcohols used for making containers and especially for making pouches for embodiments of the present invention have a glass transition temperature in the range of from 55 to 60° C., preferably 58° C., determinable according to, e.g., DIN 53765: 1994-03, or ISO 11357-2: 1999-03.

In one embodiment of the present invention, polyvinyl alcohols used for making inventive containers and especially for making pouches for embodiments of the present invention have a melting point in the range of from 185 to 187° C.

In one embodiment of the present invention, polyvinyl alcohols used for making for embodiments of the present invention and especially for making pouches comprising a single unit dose are partially acetalized or ketalized with sugars such as, glucose, fructose, or with starch. In another embodiment of the present invention polyvinyl alcohols used for making containers and especially pouches are partially esterified with, e.g., maleic acid or itaconic acid.

In one embodiment of the present invention, polyvinyl alcohol films may contain a plasticizer. Plasticizers may be used for reducing the stiffness of such polyvinyl alcohol films. Suitable compounds usable as plasticizers for polyvinyl alcohol are ethylene glycol, diethylene glycol, triethylene glycol, polyethylene glycol, for example with an average molecular weight $M_w$ up to 400 g/mol, glycerol, trimethylol propane, triethanolamine, and neo-pentyl glycol. Up to 25% by weight of the respective polyvinyl alcohol may be plasticizer.

In one embodiment of the present invention, said pouches are being made from a polymer film, said polymer being water-soluble at a temperature of at least 40° C., for example in the range of from 40 to 95° C., but insoluble in water at a temperature in the range of from 5 to 30° C. In other embodiments, said pouches are being made from polymer films that are soluble in water even at 1° C. In the context of the present invention, the terms water-soluble and soluble in water are used interchangeably. They both refer to polymers that dissolve in water at 20° C., methods of determination being discussed below. However, such polymers dissolve much slower or not detectably at all in the aqueous medium containing complexing agent (A). A polymer is deemed water-soluble if the percentage of solubility is at least 90%. A suitable method of determination of the percentage is being disclosed below.

Examples of polymer films that are soluble at 1° C. or more and of polymer films that are soluble at 40° C. are polyvinyl alcohol films available from Syntana E. Harke GmbH & Co under the trademark of Solublon®.

In one embodiment of the present invention, polymer films and preferably polyvinyl alcohol films used for making pouches that can be used in the present invention have a thickness (strength) in the range of from 10 to 100 μm, preferably 20 to 90 μm, even more preferably 25 to 35 μm. If the strength of polymer films and especially of polyvinyl alcohol films exceeds 100 μm it takes too long to dissolve them during the washing cycle. If the strength of polymer films and especially of polyvinyl alcohol films is below 10 μm they are too sensitive to mechanical stress.

In one embodiment of the present invention, the solution containing complexing agent (A) contains at least one dyestuff. Examples of dyestuffs are Acid Red 1, Acid Red 52, Acid Blue 9, Acid Yellow 3, Acid Yellow 23, Acid Yellow 73, Pigment Yellow 101, Acid Green 1, Solvent Green 7, and Acid Green 25.

In one embodiment of the present invention, the solution containing complexing agent (A) contains at least one chelating agent other than MGDA. Examples are citric acid and its respective alkali metal salts and aminopolycarboxylates and their respective alkali metal salts such as IDS and IDS-$Na_4$. In other embodiments, the solution containing complexing agent (A) does not contain any chelating agent other than MGDA.

In one embodiment of the present invention, the solution containing complexing agent (A) contains at least one viscosity modifying agent, for example one thickening agent. Examples of thickening agents are agar-agar, carragene, tragacanth, gum arabic, alginates, pectins, hydroxyethyl cellulose, hydroxypropyl cellulose, starch, gelatin, locust bean gum, cross-linked poly(meth)acrylates, for example polyacrylic acid cross-linked with methylene bis (meth)acrylamide, furthermore silicic acid, clay such as—but not limited to—montmorrilionite, zeolite, and furthermore dextrin and casein.

In a preferred embodiment of the present invention, said container and preferably such pouch contain neither peroxide nor enzyme. Such preferred embodiments usually have a longer shelf-life.

Containers and in particular pouches may be colorless. In other embodiments, they may be colored. For decorative or advertisement purposes, pictures, logos or writings may be printed on them.

Container comprising a single unit dose of a detergent composition contain at least one complexing agent (A) dissolved in an aqueous medium, said complexing agent (A) being a mixture of the L- and D-enantiomers of methyl glycine diacetic acid (MGDA) or its respective mono-, di- or trialkali metal or mono-, di- or triammonium salts, said mixture containing predominantly the respective L-isomer with an enantiomeric excess (ee) in the range of from 5 to 85%.

The expression aqueous medium as used herein refers to a medium that is liquid or gel-type at ambient temperature and that contains at least 33% by weight of water, referring to the entire continuous phase—thus, without the MGDA. In one embodiment of the present invention said aqueous medium contains at least one organic solvent miscible with water, such as, but not limited to ethylene glycol, 1,2-propylene glycol, diethylene glycol, triethylene glycol, N,N-diethanolamine, N,N-diisopropanolamine, and N-methyl N,N-diethanolamine. In other embodiments, said aqueous medium does not contain any organic solvent.

The term ammonium salts as used in the present invention refers to salts with at least one cation that bears a nitrogen atom that is permanently or temporarily quaternized. Examples of cations that bear at least one nitrogen atom that is permanently quaternized include tetramethylammonium, tetraethylammonium, dimethyldiethyl ammonium, and $n-C_{10}-C_{20}$-alkyl trimethyl ammonium. Examples of Examples of cations that bear at least one nitrogen atom that is temporarily quaternized include protonated amines and ammonia, such as monomethyl ammonium, dimethyl ammonium, trimethyl ammonium, monoethyl ammonium, diethyl ammonium, triethyl ammonium, $n-C_{10}-C_{20}$-alkyl dimethyl ammonium 2-hydroxyethylammonium, bis(2-hydroxyethyl) ammonium, tris(2-hydroxyethyl)ammonium, N-methyl 2-hydroxyethyl ammonium, N,N-dimethyl-2-hydroxyethylammonium, and especially $NH_4^+$.

In one embodiment of the present invention, complexing agents (A) are selected from mixtures of L- and D-enantiomers of molecules of general formula (I)

$$[CH_3—CH(COO)—N(CH_2—COO)_2]M_{3-x}H_x \quad (I)$$

wherein x is in the range of from zero to 0.5, preferably from zero to 0.25,

M is selected from ammonium, substituted or non-substituted, and potassium and sodium and mixtures thereof, preferably sodium. Examples of $M_{3-x}H_x$ are $Na_{3-x}H_x$, $[Na_{0.7}(NH_4)_{0.3}]_{3-x}H_x$, $[(NH_4)_{0.7}Na_{0.3}]_{3-x}H_x$, $(K_{0.7}Na_{0.3})_{3-x}H_x$, $(Na_{0.7}K_{0.3})_{3-x}H_x$, $(K_{0.22}Na_{0.78})_{3-x}H_x$, $(Na_{0.22}K_{0.78})_{3-x}H_x$, and $K_{3-x}$Hx. Preferred examples of $M_{3-x}H_x$ are selected from $Na_3$, $Na_2K$, $K_2Na$, $Na_{2.65}K_{0.35}$, $K_{2.65}Na_{0.35}$, $K_3$, $(K_{0.85}Na_{0.15})_{3-x}H_x$, and $(Na_{0.85}K_{0.15})_{3-x}H_x$.

Preferred are the trialkali metal salts of MGDA such as the tripotassium salts, the disodium monopotassium salt of MGDA, the dipotassium monosodium salt of MGDA, of trialkali metal salts wherein 20 to 25 mole-% of the alkali are potassium and the remaining 75 to 80 mole-% are sodium, of trialkali metal salts wherein 20 to 25 mole-% of the alkali metal are sodium and the remaining 75 to 80 mole-% mole-% are potassium, and of the tripotassium salt of MGDA.

In one embodiment of the present invention, the enantiomeric excess of the respective L-isomer in complexing agent (A) is in the range of from 5 to 85%, preferably in the range of from 10 to 75% and even more preferably from 20 to 60%.

In embodiments where two or more compounds of general formula (I) are present, the ee refers to the enantiomeric excess of all L-isomers present in the respective mixture compared to all D-isomers. For example, in cases wherein a mixture of the di- and trisodium salt of MGDA is present, the ee refers to the sum of the disodium salt and trisodium salt of L-MGDA with respect to the sum of the disodium salt and the trisodium salt of D-MGDA.

The enantiomeric excess can be determined by measuring the polarization (polarimetry) or preferably by chromatography, for example by HPLC with a chiral column, for example with one or more cyclodextrins as immobilized phase or with a ligand exchange (Pirkle-brush) concept chiral stationary phase. Preferred is a determination of the ee by HPLC with an immobilized optically active amine such as D-penicillamine in the presence of copper(II) salt.

In one embodiment of the present invention, complexing agent (A) may contain in the range of from 0.1 to 10% by weight of one or more optically inactive impurities, at least one of the impurities being selected from iminodiacetic acid, formic acid, glycolic acid, propionic acid, acetic acid and their respective alkali metal or mono-, di- or triammonium salts. In one embodiment of the present invention, inventive mixtures may contain less than 0.2% by weight of nitrilotriacetic acid (NTA), preferably 0.01 to 0.1% by weight. The percentages refer to total complexing agent (A).

In one embodiment of the present invention, complexing agent (A) may contain in the range of from 0.1 to 10% by weight of one or more optically active impurities, at least one of the impurities being selected from L-carboxymethylalanine and its respective mono- or dialkali metal salts, and optically active mono- or diamides that result from an incomplete saponification during the synthesis of complexing agent (A). Preferably, the amount of optically active impurities is in the range of from 0.01 to 1.5% by weight, referring to complexing agent (A). Even more preferably, the amount of optically active impurities is in the range of from 0.1 to 0.2% by weight.

In one aspect of the present invention, complexing agent (A) may contain minor amounts of cations other than alkali metal or ammonium. It is thus possible that minor amounts, such as 0.01 to 5 mol-% of total chelating agent, based on anion, bear alkali earth metal cations such as $Mg^{2+}$ or $Ca^{2+}$, or transition metal ions such as $Fe^{2+}$ or $Fe^{3+}$ cations.

In one embodiment of the present invention, the aqueous medium contains in the range of from 35 to 75% by weight of complexing agent (A), preferably 40 to 70% by weight, more preferably 45 to 70% by weight and even more preferably 48 to 65% by weight.

Aqueous medium refers to media in which the solvent is essentially water. In one embodiment, in such aqueous medium water is the sole solvent. In other embodiments, mixtures of water with one or more water-miscible solvents are used as aqueous medium. The term water-miscible solvent refers to organic solvents that are miscible with water at ambient temperature without phase-separation. Examples are ethylene glycol, 1,2-propylene glycol, isopropanol, and diethylene glycol. Preferably, at least 50% by vol of the respective aqueous medium is water, referring to the solvent.

In one embodiment of the present invention the aqueous medium containing complexing agent (A) has a pH value in the range of from pH value in the range of from 8 to 14, preferably 10.0 to 13.5.

In one embodiment of the present invention, the aqueous medium containing complexing agent (A) contains at least one inorganic basic salt selected from alkali metal hydroxides and alkali metal carbonates. Preferred examples are sodium carbonate, potassium carbonate, potassium hydroxide and in particular sodium hydroxide, for example 0.1 to 1.5% by weight. Potassium hydroxide or sodium hydroxide, respectively, may result from the manufacture of the respective complexing agent (A).

Detergent compositions comprised in inventive containers may be gel-type, liquid-type, or essentially solid. Gel-type inventive compositions may be provided as moulds. Liquid-type inventive compositions may be provided in a container having at least two compartments, one compartment containing dissolved complexing agent (A) and a second compartment containing at least one component of the dishwashing detergent composition other than complexing agent (A), such as, but not limited to a surfactant or a combination of surfactants, an enzyme or a combination of enzymes, a bleaching agent, a bleach catalyst, or a builder other than complexing agent (A).

In accordance with the above description, detergent compositions comprised in inventive containers contain ingredients other than complexing agent (A). Examples of ingredients other than complexing agent (A) are surfactants or a combination of surfactants, one or more enzymes, a bleaching agent, a bleach catalyst, or a builder other than complexing agent (A).

Detergent compositions comprised in inventive containers may contain one or more complexing agent other than MGDA. Examples for complexing agent other than MGDA are citrate, phosphonic acid derivatives, for example the disodium salt of hydroxyethane-1,1-diphosphonic acid ("HEDP"), for example trisodium citrate, and phosphates such as STPP (sodium tripolyphosphate). Due to the fact that phosphates raise environmental concerns, it is preferred that detergent compositions comprised in inventive containers are free from phosphate. "Free from phosphate" is to be understood in the context of the present invention as meaning that the content of phosphate and polyphosphate is in sum in the range from 10 ppm to 0.2% by weight, determined by gravimetric analysis and referring to the total detergent composition.

Detergent compositions comprised in inventive containers may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (II)

(II)

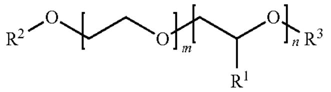

in which the variables are defined as follows:

$R^1$ is identical or different and selected from hydrogen and linear $C_1$-$C_{10}$-alkyl, preferably in each case identical and ethyl and particularly preferably hydrogen or methyl, $R^2$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$, $R^3$ is selected from $C_1$-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl.

The variables m and n are in the range from zero to 300, where the sum of n and m is at least one, preferably in the range of from 3 to 50. Preferably, m is in the range from 1 to 100 and n is in the range from 0 to 30.

In one embodiment, compounds of the general formula (II) may be block copolymers or random copolymers, preference being given to block copolymers.

Other preferred examples of alkoxylated alcohols are, for example, compounds of the general formula (III)

(III)

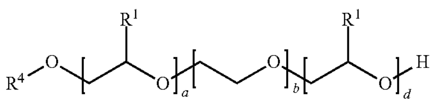

in which the variables are defined as follows:

$R^1$ is identical or different and selected from hydrogen and linear $C_1$-$C_0$-alkyl, preferably identical in each case and ethyl and particularly preferably hydrogen or methyl, $R^4$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$, a is a number in the range from zero to 10, preferably from 1 to 6, b is a number in the range from 1 to 80, preferably from 4 to 20, d is a number in the range from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (IV)

(IV)

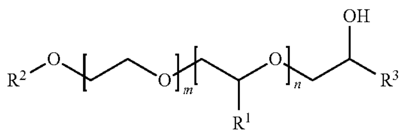

in which the variables are defined as follows:

$R^1$ is identical or different and selected from hydrogen and linear $C_1$-$C_{10}$-alkyl, preferably in each case identical and ethyl and particularly preferably hydrogen or methyl, $R^2$ is selected from $C_8$-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$, $R^3$ is selected from $C_1$-$C_{18}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The variables m and n are in the range from zero to 300, where the sum of n and m is at least one, preferably in the range of from 5 to 50. Preferably, m is in the range from 1 to 100 and n is in the range from 0 to 30.

Compounds of the general formula (III) and (IV) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglycosides such as compounds of general average formula (V) are likewise suitable.

(V)

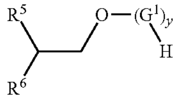

wherein:

$R^5$ is $C_1$-$C_4$-alkyl, in particular ethyl, n-propyl or isopropyl, $R^6$ is $-(CH_2)_2-R^5$, $G^1$ is selected from monosaccharides with 4 to 6 carbon atoms, especially from glucose and xylose, y in the range of from 1.1 to 4, y being an average number.

Further examples of non-ionic surfactants are compounds of general formula (VI) and (VII)

(VI)

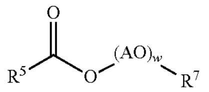

(VII)

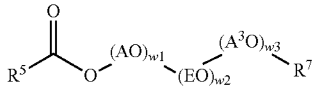

AO is selected from ethylene oxide, propylene oxide and butylene oxide,

EO is ethylene oxide, $CH_2CH_2$—O, $R^7$ selected from $C_8$-$C_{18}$-alkyl, branched or linear $A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further nonionic surfactants can be found in EP-A 0 851 023 and in DE-A 198 19 187.

Mixtures of two or more different nonionic surfactants may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (VIII)

$$R^8R^9R^{10}N\rightarrow O \quad \text{(VIII)}$$

wherein $R^{10}$, $R^8$ and $R^9$ are selected independently from each other from aliphatic, cycloaliphatic or $C_2$-$C_4$-alkylene $C_{10}$-$C_{20}$-alkylamido moieties. Preferably, $R^{10}$ is selected from $C_8$-$C_{20}$-alkyl or $C_2$-$C_4$-alkylene $C_{10}$-$C_{20}$-alkylamido and $R^8$ and $R^9$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearoic acid, oleic acid, palmitic acid, ether carboxylates, and alkylether phosphates.

In one embodiment of the present invention, detergent compositions comprised in inventive containers may contain 0.1 to 60% by weight of at least one surfactant, selected from anionic surfactants, amphoteric surfactants and amine oxide surfactants.

In a preferred embodiment, detergent compositions comprised in inventive containers do not contain any anionic surfactant.

Detergent compositions comprised in inventive containers may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Detergent compositions comprised in inventive containers compositions may comprise, for example, in the range from 3 to 10% by weight of chlorine-containing bleach.

Detergent compositions comprised in inventive containers may comprise one or more bleach catalysts. Bleach catalysts can be selected from bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Detergent compositions comprised in inventive containers may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Detergent compositions comprised in inventive containers may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, detergent compositions comprised in inventive containers comprise in total in the range from 0.1 to 1.5% by weight of corrosion inhibitor.

Detergent compositions comprised in inventive containers may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha$-$Na_2Si_2O_5$, $\beta$-$Na_2Si_2O_5$, and $\delta$-$Na_2Si_2O_5$, also fatty acid sulfonates, α-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-α-olefin, a mixture of $C_{20}$-$C_{24}$-α-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly (propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Detergent compositions comprised in inventive containers may comprise, for example, in the range from in total 10 to 70% by weight, preferably up to 50% by weight, of builder. In the context of the present invention, MGDA is not counted as builder.

In one embodiment of the present invention, such detergent compositions comprised in inventive containers may comprise one or more cobuilders.

Detergent compositions comprised in inventive containers may comprise one or more antifoams, selected for example from silicone oils and paraffin oils. In one embodiment of the present invention, detergent compositions comprised in inventive containers compositions comprise in total in the range from 0.05 to 0.5% by weight of antifoam.

Detergent compositions comprised in inventive containers may comprise one or more enzymes. Examples of enzymes are lipases, hydrolases, amylases, proteases, cellulases, esterases, pectinases, lactases and peroxidases.

In one embodiment of the present invention, detergent compositions comprised in inventive containers may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, detergent compositions comprised in inventive containers comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO.aq, $Zn(OH)_2$ and $ZnCO_3$. Preference is given to ZnO.aq.

In one embodiment of the present invention, zinc salt is selected from zinc oxides with an average particle diameter (weight-average) in the range from 10 nm to 100 μm.

The cation in zinc salt can be present in complexed form, for example complexed with ammonia ligands or water ligands, and in particular be present in hydrated form. To simplify the notation, within the context of the present invention, ligands are generally omitted if they are water ligands.

Detergent compositions comprised in inventive containers have numerous advantages. They exhibit good cleaning properties in automatic dishwashing applications. They show a good storage and shelf-life behaviour and a low tendency to colorization and especially yellowing. Complexing agent (A) shows an improved solution behavior compared to the racemic MGDA, with extremely little or no tendency to undesired precipitate formation in the container.

Another aspect of the present invention is directed towards the use of inventive containers for dishwashing or laundry cleaning. Dishwashing and laundry cleaning may refer to home care or to industrial and institutional applications, home care applications being preferred. Particularly preferred is automatic dishwash in home care applications.

Another aspect of the present invention is directed towards a process for making inventive containers comprising a single unit dose, said process also being referred to as inventive process. Another aspect of the present invention is directed towards a process for making a compartment of a container according to the present invention, hereinafter also being referred to as inventive process. The inventive process comprises several steps, hereinafter also being referred to as steps (a) to (e), and said steps briefly being summarized as follows:

(a) providing a polymer,
(b) shaping the polymer in a way that it has at least one recess so it can contain a liquid,
(c) providing a complexing agent (A) dissolved in an aqueous medium, said complexing agent (A) being a mixture of the L- and D-enantiomers of methyl glycine diacetic acid (MGDA) or its respective mono-, di- or trialkali metal or mono-, di- or triammonium salts, said mixture containing predominantly the respective L-isomer with an enantiomeric excess (ee) in the range of from 5 to 85%,
(d) placing said aqueous medium containing complexing agent (A) according to step (c) into the formed recess according to step (b),
(e) closing the open container or a compartment, respectively.

In a preferred embodiment, the container is a pouch made from a polymer film. Preferably, the polymer is polyvinyl alcohol. Steps (a) to (e) are described hereinafter in more detail.

Step (a) refers to providing a polymer, preferably a polymer film and even more preferably a film from polyvinyl alcohol.

In embodiments wherein the container or its respective compartment is different from a pouch, such polymer may have a different thickness compared to films, preferably a greater thickness. It may be in the form of granules, and step (b)—shaping the polymer—may be performed, for example, by injection molding.

In a preferred embodiment of the present invention, polymer films and preferably polyvinyl alcohol films used for making pouches for inventive compositions have a thickness (strength) in the range of from 10 to 100 μm, preferably 20 to 90 μm, even more preferably 25 to 35 μm. If the strength of polymer films and especially of polyvinyl alcohol films exceeds 100 μm it takes too long to dissolve them during the washing cycle. If the strength of polymer films and especially of polyvinyl alcohol films is below 10 μm they are too sensitive to mechanical stress.

In step (b), the polymer—preferably, the polymer film—is being shaped in a way that it has at least one recess so it can contain a liquid. Examples are thermoforming processes, especially at a temperature of 5 to 20° C. below the melting point of the respective polymer.

In embodiments wherein said container is a pouch the shaping may be performed through shaping in shaping a hose and cutting the hose into shorter pieces and closing one side each, thereby shaping sachets.

In special embodiments of the inventive process, step (b) is being performed with the aid of a forming die having at least one cavity, preferably with a plurality of cavities. Such cavities may have apertures (holes) through which reduced pressure ("vacuum") may be applied. In such special embodiments, a polymer film is being placed of the die. The polymer is then heated through a heating device. The polymer filmed is simultaneously shaped by the application of a vacuum for example through apertures of the cavity/the cavities.

In addition to applying the vacuum, it is possible to blow air or an inert gas against the polymer film in order to force it into intimate contact with the die.

In step (c), a complexing agent (A) dissolved in an aqueous medium is being provided. A way to make such solutions of complexing agent (A) is being described below.

Although it is possible to mix the respective enantiomers, for example as aqueous solutions, such method is not preferred since the synthesis of D-MGDA is tedious. It is preferred to start with L-alanine, partially neutralized, to react it with hydrocyanic acid and formaldehyde in the sense of a double Strecker synthesis and to then saponify the nitrile groups under conditions under which a partial racemization occurs.

For example, preferred are mixtures of 33 to 37 mole-% of L-alanine (free acid) and 63 to 67 mole % of the alkali metal salt of L-alanine that may be subjected to a double Strecker synthesis. Such double Strecker synthesis may be carried out by adding two moles of HCN—as free acid or as alkali metal salts—and two moles of formaldehyde in aqueous medium. The double Strecker synthesis may be carried out at a temperature in the range of from 20 to 80° C., preferably from 35 to 65° C. L-ABAN (B) is being obtained, preferably in a partially neutralized form.

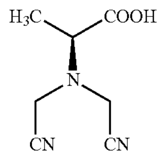

(B)

The saponification is carried out with alkali metal hydroxide. The amount—and the ratio of different alkali metals, if desired—is being set that the ratio matches the desired ratio of M in general formula (I). The saponification is then being carried out in a two-stage process, the two stages being performed at different temperatures. The first stage—during which usually no detectable racemization occurs—is carried out at a temperature in the range of from 20 to 100° C., preferably 40 to 90° C. The preferred pressure is normal pressure.

The second stage of the saponification may be performed at an average temperature in the range of from 155 to 195° C., preferably 175 to 195° C., and an average residence time in the range of from 5 to 180 minutes. Such reaction conditions are achieved at elevated pressure, for example 3 to 40 atm.

In embodiments wherein M is Na, the higher range of the temperature interval of the second stage of saponification, such as 190 to 195° C., is combined with a short residence time such as 5 to 20 minutes, or the lower range of the temperature interval of the second stage of saponification such as 155° C. to 170° C. is combined with a longer residence time such as 50 to 70 minutes, or a middle temperature such as 175 to 185° C. is combined with a middle residence time such as 21 to 49 minutes.

In embodiments wherein at least part of the alkali metal is potassium even shorter residence times are possible, for example 160° C. within a residence time of 15 to 20 minutes.

After the above synthesis, the solution of complexing agent (A) so obtained may be worked up, for example, by performing one or more purification steps. Suitable purification steps are ammonia stripping, treatment with charcoal and bleaching with peroxide.

Solutions of complexing agent (A) are obtained. Depending on the concentration in which complexing agent (A) is to be applied, the synthesis may be followed by one or more concentration steps wherein water is removed, for example by evaporation.

In step (d), aqueous medium containing complexing agent (A) so obtained is then placed into the recesses obtained in step (b). Step (d) can be performed by applying pressure or simply using gravity. Applying pressure is preferred. In embodiments wherein a die with a plurality of cavities has been used, it is preferred to simultaneously place aqueous medium containing complexing agent (A) into more than one recess.

In one embodiment, the recesses are being filled completely. In other embodiments, the recesses are only being filled partially, for example 50 to 90% by volume, the latter embodiment being preferred in order to prevent spilling of aqueous medium in step (e) to follow.

In step (e) of the inventive process, the filled but still open containers are being closed. It is preferred to perform such closing step by sealing, for example heat-sealing. Other embodiments refer to gluing a closing device on the open container, for example a polymer film, preferably a film made from water-soluble polymer.

In order to achieve sealing or heat-sealing of pouches, it is preferred to provide another polymer film and place it on the die containing the shaped film containing aqueous medium containing complexing agent (A).

In other embodiments wherein sachets of polymer film have been formed and at least partially filled with aqueous medium containing complexing agent (A) they may be closed by simply applying heat to the upper rim of the sachets, for example through a heated metal device. In other embodiments containers made from polymer film may be closed by performing a chemical reaction of a sealing substance. Said chemical reaction may be promoted by applying a vacuum.

In other embodiments, steps (b), (d) and (e) are being performed as a vertical form-fill-seal route yielding envelope-shaped pouches that contain aqueous medium containing complexing agent (A).

The present invention is further illustrated by working examples.

The ee values were determined by HPLC using a Chirex 3126 column; (D)-penicillamine, 5 μm, 250×4.6 mm. The mobile phase (eluent) was 0.5 mM aqueous $CuSO_4$-solution. Injection: 10 μl, flow: 1.3 ml/min. Detection by UV light at 254 nm. Temperature: 20° C. Running time was 25 min. The ee value was determined as difference of the area% of the L- and D-MGDA peak divided by the sum of area% of L- and D-MGDA peak. Sample preparation: A 10 ml measuring flask was charged with 50 mg of test material and then filled mark with the eluent and then homogenized.

The solubility of polymer in water is determined is as follows: a pre-weighed 400 ml beaker is charged with 50 g±0.1 g of the respective polymer and 245 ml±1 ml of distilled water. The mixture so obtained is stirred by magnetic stirring for 30 minutes, ambient temperature, at 600 rounds per minute. The solution so obtained is filtered through a filtered qualitative sintered-glass filter with a maximum pore diameter of 20 μm. The water is removed from the filtrate by evaporation. The residue corresponds to the water-soluble portion. After drying at a temperature of 50° C. under vacuum the % solubility can be determined.

I. Syntheses of Mixtures of L- and D-MGDA-$Na_3$

With exception of ee values, percentages in the context of the examples refer to percent by weight unless expressly indicated otherwise.

I.1 Synthesis of a Solution of Partially Neutralized of L-Alanine

A 5-litre stirred flask was charged with 2,100 g of de-ionized water and heated to 40° C. 1,200 g of L-alanine (13.47 mol, 98% ee) were added. To the resultant slurry 700 g of 50% by weight aqueous sodium hydroxide solution (8.75 mol) were added over a period of 30 minutes. During the addition the temperature raised to 60° C. After complete addition of the sodium hydroxide the slurry was stirred at 60° for 30 minutes. A clear solution was obtained.

I.2 Synthesis of Aqueous Solutions of Complexing Agents (A.1), (A.2) and (A.3)

The continuous syntheses of ca. 40% solutions of complexing agents (A.1) to (A.3) were carried out in cascade of 6 stirred tank reactors, total volume of 8.51. The reaction mixture passed all 6 stirred tank reactors (STR.1 to STR.6) consecutively. The last stirred tank reactor to be passed, STR.6, was connected to a tubular reactor, TR.7. In the first three stirred tank reactors, STR.1 to STR.3, the double Strecker synthesis was carried out, and STR.1 to STR.3 were operated at 40° C. The average residence time in STR.1 to STR.3 was 45 to 90 min in total. In the three stirred tank reactors STR.4 to STR.6 the saponification was carried out. STR.4 to STR.6 were operated at 60° C. The average residence time in STR.4 to STR.6 was 150 to 400 min in total.

The saponification was then completed in tubular reactor TR.7 which was operated with a temperature profile of 130 to 195° C. The final ammonia stripping is done in a column under normal pressure using steam. Formaldehyde (30% aqueous solution), an aqueous solution of L-alanine (I) and its sodium salt obtained according to 1.1 and 80 mol-% of the required HCN were added to STR.1, the remaining 20% of the required HCN were added to STR.2, the required sodium hydroxide solution was added in STR.4.

The molar ratios of the feed materials were as follows:

Sum of L-alanine and its sodium salt: 1.00,
Formaldehyde=1.95 to 2.05,
HCN=1.95 to 2.10 and
Sodium hydroxide=3.15 (total amount of sodium hydroxide, including sodium hydroxide added in step (1.1).

The 40% by weight solutions of complexing agent (A) displayed excellent olfactory behavior, and they had a low tendency of yellowing, especially after treatment with charcoal or bleaching with hydrogen peroxide.

TABLE 1

Influence of temperature and residence time of second saponification step

| | Temperature [° C.] | Residence time for second saponification step [min] | ee [%] |
|---|---|---|---|
| (A.1) | 180 | 70 | 10.0 |
| (A.2) | 180 | 30 | 30.6 |
| (A.3) | 178 | 30 | 36.2 |

The concentration of the solutions was raised by evaporation of water at 70° C. until the concentration was 50%.

II. Manufacture of Inventive Pouches

A polyvinyl alcohol film, degree of saponification: 88 mole-%, thickness 25 μm, is being placed over a die having 6 hemisphere-shaped cavities with a volume of 0.5 ml each.

By application of manual pressure, recesses may be formed, one per cavity. With a pipette, 7 to 8 drops of solution of complexing agent (A.1), (A.2) or (A.3) are placed into each recess (1 ml corresponds to 20 drops). Then, another polyvinyl alcohol film, thickness 25 μm, is being placed over the first die. By application of heat, namely, 180° C., or vacuum, each for a short time such as 1 to 5 seconds the recesses are being sealed. The filled pre-shaped pouches can then be cut out manually. Inventive pouches that serve as a compartment are being obtained. They contain a solution of the respective complexing agent (A.1) to (A.3). Even upon storage in a refrigerator at 5° C., no precipitation of solids from the solution can be observed.

III. Manufacture of Detergent Compositions

Example detergent compositions according to Table 2 are being prepared by mixing the respective ingredients in dry state.

TABLE 2

Example detergent compositions for automatic dishwashing

| | All amounts in g/sample | | |
|---|---|---|---|
| | ADW.1 | ADW.2 | ADW.3 |
| Protease | 2.5 | 2.5 | 2.5 |
| Amylase | 1 | 1 | 1 |
| n-$C_{18}H_{37}$—$O(CH_2CH_2O)_9H$ | 5 | 5 | 5 |
| Polyacrylic acid $M_w$ 4000 g/mol as sodium salt, completely neutralized | 10 | 10 | 10 |
| Sodium percarbonate | 10.5 | 10.5 | 10.5 |
| TAED | 4 | 4 | 4 |
| $Na_2Si_2O_5$ | 2 | 2 | 2 |
| $Na_2CO_3$ | 19.5 | 19.5 | 19.5 |
| Sodium citrate dihydrate | 15 | 22.5 | 30 |
| HEDP | 0.5 | 0.5 | 0.5 |

A tablet may be formed of any of the above mixture, weight: 18 g, and one pouch from (II) may be placed on each tablet. The tablets are being packed—together with the pouch—into a film of polyvinyl alcohol, degree of saponification: 88 mole-%, thickness: 35 μm. They are being used as unit doses in an automatic dishwasher and yield excellent dishwashing results. Their use is convenient.

When racemic MGDA-$Na_3$ is used instead of the non-racemic mixture applied above, after a few hours precipitate formation can be observed in the pouch wherein the MGDA is.

The invention claimed is:

1. A container comprising a single unit dose of a detergent composition containing at least one complexing agent (A) dissolved in an aqueous medium, said complexing agent (A) being a mixture of the L- and D-enantiomers of methyl glycine diacetic acid (MGDA) or its respective mono-, di- or trialkali metal or mono-, di- or triammonium salts, said mixture containing predominantly the respective L-isomer with an enantiomeric excess (ee) in the range of from 5 to 85%, wherein said container is made from a polymer, and wherein such aqueous medium comprises at least 33% by weigh of water, referring to the entire continuous phase.

2. The container according to claim 1, wherein said container encompasses two or more compartments.

3. The container according to claim 1, wherein said container is mechanically flexible or stiff.

4. The container according to claim 1, wherein said container is in the form of a box with one or more compartments or in the form of a sachet with one or more compartments or in the form of a pouch with one or more compartments or in the form of a combination of a box and a pouch.

5. The container according to claim 4, in the form of the pouch or in the form of the combination of the box and the pouch, the pouch being made from a polymer film, said polymer being water-soluble in water at a temperature of at least 1° C.

6. The container according to claim 1, comprising at least two compartments wherein one compartment contains complexing agent (A) in aqueous medium and at least one further compartment contains an essentially solid composition.

7. The container according to claim 1, wherein the complexing agent (A) is selected from the group consisting of a mixture of L- and D-isomers of the trisodium salt of MGDA, of the disodium monopotassium salt of MGDA, of the dipotassium monosodium salt of MGDA, of trialkali metal salts wherein 20 to 25 mole-% of the alkali are potassium and the remaining 75 to 80 mole-% are sodium, of trialkali metal salts wherein 20 to 25 mole-% of the alkali metal are sodium and the remaining 75 to 80 mole-% mole-% are potassium, and of the tripotassium salt of MGDA.

8. The container according to claim 1, wherein said aqueous medium contains in the range of from 35 to 75% by weight of the complexing agent (A).

9. The container according to claim 1, wherein said aqueous medium additionally contains at least one dyestuff.

10. The container according to claim 1, wherein the polymer is polyvinyl alcohol.

11. The container according to claim 1, wherein said container comprises at least two compartments, wherein said detergent additionally comprises an inorganic peroxide, said inorganic peroxide not being in the compartment containing the aqueous medium containing complexing agent (A).

12. The container according to claim 1, wherein the container is a pouch made from a polymer film.

13. A method for dishwashing or laundry cleaning, comprising arranging the container according to claim 1 such that the detergent composition contacts dishes or laundry.

14. A process for making the container according to claim 1, said process comprising the steps of (a) providing a polymer, (b) shaping the polymer in a way that it has at least one recess so it can contain a liquid, (c) providing a complexing agent (A) dissolved in an aqueous medium, said complexing agent (A) being a mixture of the L- and D-enantiomers of methyl glycine diacetic acid (MGDA) or its respective mono-, di- or trialkali metal or mono-, di- or triammonium salts, said mixture containing predominantly the respective L-isomer with an enantiomeric excess (ee) in the range of from 5 to 85%, (d) placing said aqueous medium containing complexing agent (A) according to step (c) into the formed recess according to step (b), (e) closing the open container or compartment, respectively.

15. The process according to claim 14 wherein the polymer is provided in the form of a polymer film.

16. The process according to claim 14 wherein step (e) is being performed by sealing.

17. The process according to claim 14, wherein step (b) is being performed with the aid of a forming die having at least one cavity.

* * * * *